United States Patent [19]
Nixon et al.

[11] Patent Number: 5,928,885
[45] Date of Patent: *Jul. 27, 1999

[54] KIT FOR DETECTING ALZHEIMER'S DISEASE

[75] Inventors: Ralph A. Nixon, Arlington, Mass.; Ken-Ichi Saito, Yokahama, Japan

[73] Assignee: The McLean Hospital Corporation, Belmont, Mass.

[*] Notice: This patent is subject to a terminal disclaimer.

[21] Appl. No.: 08/681,375

[22] Filed: Jul. 23, 1996

Related U.S. Application Data

[63] Continuation of application No. 08/184,603, Jan. 24, 1994, Pat. No. 5,624,807, which is a continuation of application No. 08/095,319, Jul. 22, 1993, abandoned, which is a continuation-in-part of application No. 07/925,594, Jul. 22, 1992, abandoned.

[51] Int. Cl.$^6$ ............... G01N 33/573; C07K 16/00; C12P 21/08
[52] U.S. Cl. ............ 435/7.4; 435/967; 435/975; 436/518; 530/387.1; 530/388.1; 530/388.26
[58] Field of Search ............ 435/975, 7.1, 7.4, 435/7.92, 7.93, 7.94, 7.95, 967; 436/518, 524, 528, 530, 531; 530/357.1, 388.1, 388.26

[56] References Cited

U.S. PATENT DOCUMENTS 5,134,062  7/1992  Blass .

FOREIGN PATENT DOCUMENTS

WO 93/02106  2/1993  WIPO .

OTHER PUBLICATIONS

Adunsky, A. et al., "Increased cytosolic free calcium in lymphocytes of Alzheimer patients," *J. Neuroimmunol.* 33:167–172 (Jul. 1991).

Colvin, R. A. et al., "Na$^+$/Ca$^{2+}$ exchange activity is increased in Alzheimer's disease brain tissues," *Brain Res.* 543:139–147 (Mar. 1991).

Dure, Leon S. IV et al., "Excitatory Amino Acid Binding Sites in the Caudate Nucleus and Frontal Cortex of Huntington's Disease," *Ann. Neurol.* 30:785–793 (Dec. 1991).

Elce, J. S. et al., "Calpain I activation is not correlated with aggregation in human platelets," *Biochem J.* 261:1039–1042 (1989).

Ham, R. G. and W. L. McKeehan, "Development of Improved Media and Culture Conditions for Clonal Growth of Normal Diploid Cells," *In Vitro* 14(1):11–22 (1978).

Imajoh, S. et al., "Molecular Cloning of the cDNA for the Large Subunit of the High–Ca$^{2+}$–Requiring Form of Human Ca$^{2+}$–Activated Neutral Protease," *Biochem.* 27:8122–8128 (1988).

Inomata, M. et al., "Autolytic Activation of Calcium–Activated Neutral Protease," *Biochem. Biophys. Res. Comm.* 138(2):638–643 (1986).

Inomata, M. et al., "Purification and Characterization of a Calcium–Activated Neutral Protease from Rabbit Skeletal Muscle which Requires Calcium Ions of $\mu$M Order Concentration," *J. Biochem.* 93:291–294 (1983).

Inomata, M. et al., "Properties of Erythrocyte Membrane Binding and Autolytic Activation of Calcium–activated Neutral Protease," *J. Biol. Chem.* 264(31):18838–18843 (1989).

Iwamoto, N. et al., "Localization of calpain immunoreactivity in senile plaques and in neurones undergoing neurofibrillary degeneration in Alzheimer's disease," *Brain Res.* 561:177–180 (Oct. 1991).

Joachim, C. L. et al., "Amyloid β–protein deposition in tissues other than brain in Alzheimer's disease," *Nature* 341:226–230 (1989).

Kawashima, S. et al., "Transglutaminase and Calcium–protease Activities in Alzheimer's Disease Brain," *Biomed. Res.* 10(1):17–23 (1989).

Mantle, D. and E. K. Perry, "Comparison of Ca$^{2+}$–activated proteinase enzyme and endogenous inhibitor activity in brain tissue from normal and Alzheimer's disease cases," *J. Neurol. Sci.* 102:220–224 (Jul. 1991).

Marotta, C. A., "Molecular Biology of Neuronal Aging," *Department of Health and Human Services Grant Application,* executed Jun. 1986, funded before 1990.

Morris, J. C. et al., "The Consortium to Establish a Registry for Alzheimer's Disease (CERAD). Part I. Clinical and neuropsychological assessment of Alzheimer's disease," *Neurol.* 39:1159–1165 (1989).

Murachi, T., "Intracellular Regulatory System Involving Calpain and Calpastatin," *Biochem. Int.* 18(2):263–294 (1989).

Nee, L. E. et al., "A Family With Histologically Confirmed Alzheimer's Disease," *Arch. Neurol.* 40:203–208 (1983).

Nilsson, E. et al., "Calpain and Calpastatin in Normal and Alzheimer–Degenerated Human Brain Tissue," *Neurobiol. Aging* 11:425–431 (1990).

Nixon, R. A. et al., "Calcium–Activated Neutral Proteinases as Regulators of Cellular Function: Implications for Alzheimer's Disease Pathogenesis," *Ann. New York Acad. Sci.*568:198–208 (1989).

Nixon, R. A., "Proteolysis in Normal and Pathological Axons and Glia," *Department of Health and Human Services Grant Application,* executed Jun. 1982, funded before 1990.

(List continued on next page.)

*Primary Examiner*—Paula K. Hutzell
*Assistant Examiner*—Patricia A. Duffy
*Attorney, Agent, or Firm*—Sterne, Kessler, Goldstein & Fox, P.L.L.C.

[57] ABSTRACT

Methods for screening individuals for Alzheimer's disease are disclosed. Also disclosed are antibodies that immunochemically react with the isoforms of calcium-activated neutral proteinases which are characteristic of Alzheimer's disease. Also disclosed are methods for screening drugs which are useful in treating or preventing Alzheimer's disease.

3 Claims, 6 Drawing Sheets

OTHER PUBLICATIONS

Nixon, R. A., "Human Brain Proteolysis in Aging and Alzheimer's Disease," *Department of Health and Human Services Grant Application*, executed Sep. 1983, funded before 1990.

Nixon, R. A., "Human Brain Proteolysis in Aging and Alzheimer's Disease," *Department of Health and Human Services Grant Application*, executed Oct. 1986, funded before 1990.

O'Brien, R. A. D. et al., "Protease Inhibitors Reduce the Loss of Nerve Terminals Induced by Activity and Calcium in Developing Rat Soleus Muscles In Vitro," *Neurosci.* 12(2):637–646 (1984).

Perlmutter, L. S. et al., "The Ultrastructural Localization of Calcium–Activated Protease "Calpain" in Rat Brain," *Synapse* 2:79–88 (1988).

Perlmutter, L. S. et al., "Distribution of Calcium–Activated Protease Calpain in the Rat Brain," *J. Comparative Neurol.* 296:269–276 (1990).

Peterson, C. et al., "Altered Calcium Uptake in Cultured Skin Fibroblasts from Patients with Alzheimer's Disease," *New Eng. J. Med.* 312(16):1063–1064 (1985).

Peterson, C. et al., "Increased spectrin proteolysis in fibroblasts from aged and Alzheimer donors," *Neurosci. Lett.* 121:239–243 (Jan. 1991).

Pontremoli, S. et al., "Activation by Hemoglobin of the $Ca^{2+}$–Requiring Neutral Proteinase of Human Erythrocytes: Structural Requirements," *Biochem. Biophys. Res. Comm.* 123(1):331–337 (1984).

Saido, T. C. et al., "Autolytic Transition of $\mu$–Calpain upon Activation as Resolved by Antibodies Distinguishing between the Pre– and Post–Autolysis Forms," *J. Biochem.* 111(1):81–86 (Jan. 1992).

Saido, T. C. et al., "Proteolysis of protein kinase C by calpain: Effect of acidic phopholipids," *Biomed. Biochim. Acta* 50:485–489 (Nov. 1991).

Saito, K.–I. et al., "Widespread activation of calcium–activated neutral proteinase (calpain) in the brain in Alzheimer disease: A potential molecular basis for neuronal degeneration," *Proc. Natl. Acad. Sci. USA* 90:2628–2632 (1993).

Saitoh, T. et al., "Biology of Disease: Protein Kinases and Phosphorylation in Neurologic Disorders and Cell Death," *Lab. Invest.* 64(5):596–616 (May 1991).

Samis, J. A. et al., "Calpain I remains intact and intracellular during platelet activation," *Biochem. J.* 246;:481–488 (1987).

Sevier, E. D. et al., "Monoclonal Antibodies in Clinical Immunology," *Clin. Chem.* 27(11):1797–1806 (1981).

Siman, R. et al., "Proteolytic Processing of β–Amyloid Precursor by Calpain I," *J. Neurosci.* 10(7):2400–2411 (1990).

Siman, R., "Role of Calpain I in Excitatory Amino Acid–Induced Degenerative Structural Changes," in: *Neurotoxicity of Excitatory Amino Acids*, Guidotti, A. ed., Raven Press: New York (1990).

Swanson, G. J. and G. Vrbová, "Effects of low calcium and inhibition of calcium–activated neutral protease (CANP) on mature nerve terminal structure in the rat sternocostalis muscle," *Dev. Brain Res.* 33:199–203 (1987).

Takeuchi, K. H. et al., "Immunoassay and Activity of Calcium–Activated Neutral Proteinase (mCANP): Distribution in Soluble and Membrane–Associated Fractions in Human and Mouse Brain," *J. Neurochem.* 58(4):1526–1532 (Apr. 1992).

Tanzi, R. E. et al., "The genetic defect in familial Alzheimer's disease is not tightly linked to the amyloid β–protein gene," *Nature* 329:156–157 (1987).

Tanzi, R. E. et al., "Amyloid β Protein Gene: cDNA, mRNA Distribution, and Genetic Linkage Near the Alzheimer Locus," *Science* 235:880–884 (1987).

Tanzi, R. E. et al., "Protease inhibitor domain encoded by an amyloid protein precursor mRNA associated with Alzheimer's disease," *Nature* 331:528–530 (1988).

Vitto, A. and R. A. Nixon, "Calcium–Activated Neutral Proteinase of Human Brain: Subunit Structure and Enzymatic Properties of Multiple Molecular Forms," *J. Neurochem.* 47(4):1039–1051 (1986).

Willers, I. et al., "Growth Studies on Fibroblasts of Patients with Autosomal Recessive Friedreich's Ataxia," *Pathobiol.* 59:357–360 (Jun. 1991).

Winker, M. A., "Tacrine for Alzheimer's Disease: Which Patient, What Dose?," *J. Amer. Med. Assoc.* 271(13):1023–1024 (1994).

Zimmerman, U.–J. P. and W. W. Schlaepfer, "Two–stage autolysis of the catalytic subunit initiates activation of calpain I," *Biochim. Biophys. Acta* 1078:192–198 (Jun. 1991).

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
       (A) LENGTH: 21 amino acids
       (B) TYPE: amino acid
       (D) TOPOLOGY: linear (xi) SEQUENCE DESCRIPTION: SEQ ID NO:1:

Ala Gly Ile Ala Ala Lys Leu Ala Lys Asp Arg Glu Ala Ala Glu Gly
   1               5                   10                  15

Leu Gly Ser His Glu
               20

(2) INFORMATION FOR SEQ ID NO:2:

(i) SEQUENCE CHARACTERISTICS:
       (A) LENGTH: 34 amino acids
       (B) TYPE: amino acid
       (D) TOPOLOGY: linear (xi) SEQUENCE DESCRIPTION: SEQ ID NO:2:

Ser Glu Glu Ile Ile Thr Pro Val Tyr Cys Thr Gly Val Ser Ala Gln
   1               5                   10                  15

Val Gln Lys Gln Arg Ala Arg Glu Leu Gly Leu Gly Arg His Glu Asn
               20                  25                  30

Ala Ile

KIT FOR DETECTING ALZHEIMER'S DISEASE

CROSS-REFERENCE TO RELATED APPLICATIONS

The present application is a continuation of U.S. application Ser. No. 08/184,603, filed Jan. 24, 1994, now U.S. Pat. No. 5,624,807 which is a continuation of U.S. application Ser. No. 08/095,319, filed Jul. 22, 1993, abandoned, which is a continuation-in-part of U.S. application Ser. No. 07/925,594, filed Jul. 22, 1992, now abandoned, the contents of all three applications being fully incorporated by reference herein.

The present invention was made with U.S. government support. Therefore, the U.S. government has certain rights in the invention.

FIELD OF THE INVENTION

The present invention relates to the field of medical diagnostics employing antibodies to screen patients for Alzheimer's disease.

BACKGROUND OF THE INVENTION

Synaptic loss and neuronal cell death correlate strongly with the degree of cognitive impairment in Alzheimer disease (Terry et al., *Ann. Neurol.* 30:572–580 (1991); Hamos et al., *Ann. Neurol.* 39: 355 (1991); Dekosky & Scheff, *Ann. Neurol.* 27:457–464 (1990)). These pathologic events are not yet defined at the biochemical level although many putative etiologic factors in Alzheimer disease share in common the potential for disrupting cellular calcium homeostasis (Khachaturian, Z. S., *Aging* 1(1):17–34 (1989)), and some evidence exists for such disruption in Alzheimer tissues (Colvin, R. A., et al., *Brain Res.* 543:139–147 (1991); Peterson, C., et al., *N. Engl. J. Med.* 312(16):1063–1064 (1985); Peterson & Goldman, *Proc. Natl. Acad. Sci. USA* 83:2758–2762 (1986); Rizopoulos, E., et al., *Brain Res. Bull.* 21:825–828 (1988); Peterson, C., et al., *Neurosci. Lett.* 121:239–243 (1991); Iacopino & Christakos, *Proc. Natl. Acad. Sci. USA* 87:4078–4082 (1990); Gibson, G. E., et al., *Biol. Psychiatry* 22:1079–1086 (1987)).

Calcium-activated neutral proteinases (CANP) are a family of proteases implicated in regulating aspects of signal transduction (Pontremoli, S., et al., *Proc. Natl. Acad. Sci. USA* 87:3705–3707 (1990); Piggott, M. A., et al., *Brain Res.* 565:42–47 (1991); Adunsky, A., et al., *J. Neuroimmunology* 33:167–172 (1991); Suzuki & Ohno, *Cell Struct. Funct.* 15:1–6 (1990); Murachi, T., *Biochem. Internatl.* 18(2): 263–294 (1989)). Limited proteolysis by CANPs is involved in regulating important enzymes, including calcium-dependent protein kinases and protein phosphatases and neurotransmitter enzymes, and in modifying the function of structural proteins of the membrane and membrane skeleton (Togari, A., et al., *Biochem. Biophys. Res. Commun.* 134(2) :749–754 (1968); Kishimoto, A., et al., *J. Biol. Chem.* 258:1156–1164 (1983); Tallant, E. A., et al., *Biochem.* 27:2205–2211 (1988); Nixon, R. A., *Ann. N.Y. Acad. Sci.* 568:198–208 (1989)). Massive activation of CANPs, as occurs in excitatoxicity and ischemia, induces rapid irreversible neuronal injury (Siman, R., et al., *J. Neurosci.* 9:1579–1590 (1989); Siman, R., in *Neurotoxicity of Excitatory Amino Acids*, A. Guidotti, ed., Raven Press, New York, pp. 145–161 (1990); Lee, K. S., et al., *Proc. Natl. Acad. Sci. USA* 88:7233–7347 (1991)). However, previous reports indicate that total CANP activity is not significantly altered in Alzheimer brain (Kawashima, S., et al., *Biomed. Res.* 10(1):17–23 (1989); Mantle & Perry, *J. Neurol. Sci.* 102:220–224 (1991); Nilsson, E., et al., *Neurobiol. Aging* 11:425–431 (1990)).

CANP exists in cells principally as an inactive precursor isoform (Suzuki & Ohno, *Cell Struct. Funct.* 15:1–6 (1990); Suzuki, K., et al., *FEBS Lett.* 220:271 (1987)), which is activated by autoproteolytic cleavage of an amino-terminal sequence in the presence of calcium (Suzuki, K., et al., *J. Biochem.* 90:1787–1793 (1981); Inomata, M., et al., *J. Biochem.* 98:407–416 (1985); Zimmerman & Schlaepfer, *Biochim. Biophys. Acta* 1078:192–198 (1991); Suzuki, K., et al., *FEBS Lett.* 220:271 (1987)). The action of CANP in vivo has been difficult to monitor by in vitro enzyme assay because the precursor form is also activated by the assay procedure, and activities are, in turn, influenced by instability of the enzyme as well as by various cytosolic inhibitory and activating factors (Mellgren & Murachi, eds., *Intracellular Calcium-dependent Proteolysis*, CRC Press, Boston, Mass., pp. 1–276 (1990)).

SUMMARY OF THE INVENTION

To circumvent some of these problems, we identified distinct isoforms of $\mu$CANP in postmortem human brain that correspond to the autolytically activated isoform and the uncleaved precursor previously demonstrated in erythrocytes. The invention relates to the discovery that the ratio of precursor to activated isoforms of $\mu$CANP in tissues provides an index of CANP function in vivo.

In particular, the invention relates to a method for the detection of Alzheimer's disease in an individual, comprising
(a) obtaining a tissue sample from an individual suspected of having Alzheimer's disease; and
(b) determining the relative ratio of the active 76-kDa isoform of $\mu$CANP to the 80-kDa isoform in said tissue sample;
wherein an increased ratio of 76-kDa/80-kDa compared to a control group of individuals not having Alzheimer's disease confirms that the individual suspected of having Alzheimer's disease does have Alzheimer's disease.

The invention also relates to a method for the detection of Alzheimer's disease in an individual, comprising
(a) obtaining a tissue sample from an individual suspected of having Alzheimer's disease; and
(b) determining the relative ratio of the active 76-kDa isoform of $\mu$CANP to the total quantities of the 76-kDa, 78-kDa and 80-kDa isoforms;
wherein an increased ratio of 76-kDa/76-kDa+78-KDa+80-kDa compared to a control group of individuals not having Alzheimer's disease confirms that the individual suspected of having Alzheimer's disease has Alzheimer's disease.

The invention also relates to a kit which is useful for detecting Alzheimer's disease in a individual suspected of having the disease, comprising a carrier means having in close confinement therein one or more container means, wherein a first container means contains a detectable antibody that is specific for the active 76-kDa isoform of $\mu$CANP and the 80-kDa isoform of $\mu$CANP. Further container means may contain a detectably labelled antibody that is immunoreactive with said detectable antibody that is specific for the active 76-kDa isoform of $\mu$CANP and the 80-kDa isoform of $\mu$CANP. In addition, further container means may contain a means for separating the 76-kDa isoform of $\mu$CANP and the 80-kDa isoform of $\mu$CANP.

The invention also relates to a kit which is useful for detecting Alzheimer's disease in a individual suspected of having the disease, comprising a carrier means having in close confinement therein two or more container means, wherein a first container means contains a first detectable antibody that is immunoreactive with the 80-kDa isoform of μCANP and is not immunoreactive with the 76-kDa and 78-kDa isoforms of μCANP and a second container means contains a second detectable antibody that is immunoreactive with the 76-kDa, 78-kDa and 80-kDa isoforms of μCANP. Preferably, the first and second detectable antibodies are detectably labelled with different labels that can be discriminated on detection.

The invention also relates to a method for screening a drug for use in the treatment or prevention of Alzheimer's disease, comprising (a) obtaining a first animal brain sample;

(b) determining the relative ratio of the active 76-kDa isoform of μCANP to the 80 kDa isoform in the first animal brain sample;

(c) incubating a second animal brain sample with an aqueous solution of $Ca^{++}$ and a drug suspected of being useful in treating or preventing Alzheimer's disease;

(d) determining the relative ratio of the active 76-kDa isoform of μCANP to the 80 kDa isoform in the tissue sample obtained in step (c);

wherein when the 76-kDa/80-kDa ratio of the animal brain sample contacted with said drug as determined in step (d) is reduced compared to the 76-kDa/80-kDa ratio obtained in step (b) confirms that the drug is useful for treating or preventing Alzheimer's disease.

The invention also relates to a method for screening a drug for use in the treatment or prevention of Alzheimer's disease, comprising (a) obtaining a first fibroblast sample from an animal;

(b) determining the relative ratio of the active 76-kDa isoform of μCANP to the 80 kDa isoform in the first fibroblast sample;

(c) incubating a second fibroblast sample with an aqueous solution of $Ca^{++}$, a calcium ionophore, and a drug suspected of being useful in treating or preventing Alzheimer's disease;

(d) determining the relative ratio of the active 76-kDa isoform of μCANP to the 80 kDa isoform in the fibroblast sample obtained in step (c);

wherein when the 76-kDa/80-kDa ratio of the fibroblast sample contacted with said drug as determined in step (d) is reduced compared to the 76-kDa/80-kDa ratio obtained in step (b) confirms that the drug is useful for treating or preventing Alzheimer's disease.

DESCRIPTION OF THE FIGURES

FIGS. 5(A–C) depict bar graphs showing the μCANP isoform ratios (76 kDa/80 kDa) in brain regions from control, Alzheimer and Huntington disease (HD) brains.

DESCRIPTION OF THE PREFERRED EMBODIMENTS

Figure 1A:
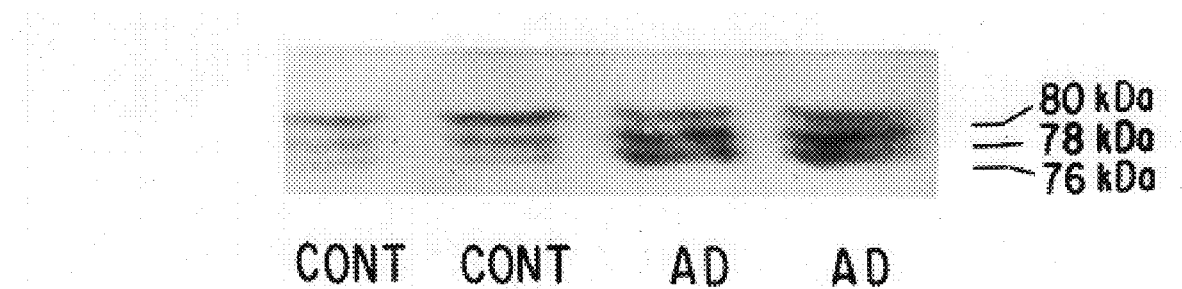
FIG. 1(A) depicts an immunoblot analysis of μCANP in prefrontal cortex from two control (CONT) and two Alzheimer (AD) patients.

Calcium-activated neutral proteinases (CANP) are key enzymes in intra-cellular signaling cascades and are potential mediators of calcium-induced cell injury. The enzyme form requiring micromolar calcium levels (μCANP), which is enriched in neurons, has been most frequently implicated. As an index of changes in the in vivo activity of μCANP, the ratios of the activated isoform of μCANP to the precursor isoforms were measured immunochemically in regions of postmortem human brain. This ratio was elevated 3-fold in the prefrontal cortex from patients with Alzheimer disease but not from those with Huntington disease. Other regions of Alzheimer brain (putamen and cerebellum) where neuronal degeneration is considered minimal in Alzheimer disease also displayed significantly increased μCANP activation.

Thus, the invention relates to the discovery that elevated levels of the active isoform of μCANP is associated with Alzheimer's disease. In a first aspect, the invention relates to a method for the detection of Alzheimer's disease in an individual, comprising (a) obtaining a tissue sample from an individual suspected of having Alzheimer's disease; and (b) determining the relative ratio of the active 76-kDa isoform of μCANP to the 80-kDa isoform in said tissue sample;

wherein an increased ratio of 76-kDa/80-kDa compared to a control group of individuals not having Alzheimer's disease confirms that the individual suspected of having Alzheimer's disease does have Alzheimer's disease.

The tissue sample may be a brain biopsy or, more preferably, a fibroblast sample. Where a brain biopsy sample is obtained, it preferably obtained from the frontal cortex, putamen or cerebellum. When obtained from the frontal cortex, it is possible to discriminate between Alzheimer's disease and Huntington's disease. When nervous system tissue is analyzed according to the present invention, about 0.1 to about 0.5 g of tissue is needed to carry out the analysis.

Most preferably, a sample of fibroblasts is obtained from an individual suspected of having Alzheimer's disease. Fibroblasts may be obtained from individuals according to the procedure described by Willers, I. et al., *Pathobiology* 59:357–360 (1991), the disclosure of which is fully incorporated by reference herein. See also Ham and McKeehan, *In Vitro* 14:11–22 (1978), who teach methods for growing fibroblasts in cell culture. About 0.05 to about 0.1 g of fibroblasts is needed to carry out the analysis.

After obtaining the tissue sample, it is homogenized in a physiological buffer, centrifuged and the supernatant tested for the 76-kDa and 80-kDa isoforms of μCANP. Preferably, the supernatant is first subjected to fractionation to remove potential interfering substances. This may be carried out by applying the supernatant to a DEAE-cellulose column, and eluting the column with a buffer containing increase amounts of a salt such as potassium chloride.

The fractions eluting off the column may be subject to electrophoresis to separate the 76-kDa, 78-kDa and 80-kDa isoforms, followed by electrotransfer to a membrane (e.g., nitrocellulose) and immunoblot analysis with detectable antibodies that are immunoreactive with one or more of the 76-kDa, 78-kDa and 80-kDa isoforms. The detectable antibody may be detectably labelled as described herein or may be detected by contacting with a second antibody that is immunoreactive therewith, e.g. where the first antibody is from a first animal species and the second antibody is from a second animal species and is immunoreactive with the antibodies from the first animal species. Antibodies which are immunoreactive with the 76-kDa, 78-kDa and 80-kDa isoforms, are taught, for example, by Samis, J. A., et al., *Biochem. J.* 246:481–488 (1987); and Elce, J. S., et al., *Biochem. J.* 261:1039–1042 (1989), the contents of which are fully incorporated by reference herein. It is also possible to employ antibodies that are selective for only the 76-kDa isoform. See Saido, T. C. et al., *J. Biochem.* 111:81–86 (1992), the disclosure of which is fully incorporated by reference herein.

More preferably, the ratio of 76-kDa and 80-kDa isoforms is determined with detectably labelled antibodies that discriminate between the 80-kDa isoform and the 76-kDa and 78-kDa isoforms. When the 80-kDa isoform is converted to the 76-kDa and 78-kDa isoforms by proteolysis, the N-terminus of the 80-kDa isoform is lost. Thus, it is possible to raise a first antibody to the N-terminal region of the 80-kDa isoform to obtain an antibody that is immunochemically reactive only with the 80-kDa isoform. A second antibody, which is immunochemically reactive with the 76-kDa, 78-kDa and 80-kDa isoforms can be used to quantitate total μCANP. Since the amount of the 78-kDa isoform does not change significantly in Alzheimer diseased brain, the ratio of the second antibody to the first antibody correlates to the ratio of the 76-kDa to 80-kDa isoforms.

Preferably, the first antibody is raised against a region in the first 21 N-terminal amino acids of μCANP. The amino acid sequence of μCANP is taught by Imajoh, S. et al., *Biochem.* 27:8122–8128 (1988), the contents of which are fully incorporated by reference herein. Given the amino acid sequence of μCANP, it is possible to obtain N-terminal fragments of μCANP and prepare monoclonal or polyclonal antibodies thereto. For example, one may prepare peptide segments of 8 amino acids or more by means of solid phase synthesis, conjugate the peptide segments to an immunogenic carrier, an immunize an animal therewith. Larger peptide fragments are capable of inducing, per se, an immune response. However, since many small molecules do not induce active immunity by themselves, it may be necessary to conjugate the peptides to an immunogenic carrier to induce production of antibodies thereto. Such immunogenic carriers include, but are not limited to, proteins such as bovine serum albumin, diphtheria toxoid, tetanus toxoid, edestin, keyhole-limpet hemocyanin, Pseudomonal Toxin A, choleragenoid, cholera toxin, pertussis toxin, viral proteins, and eukaryotic proteins such as interferons, interleukins, or tumor necrosis factor. Such proteins may be obtained from natural or recombinant sources according to methods known to those skilled in the art. When obtained from recombinant sources, the immunogenic carrier may comprise a protein fragment comprising at least the immunogenic portion of the molecule. Other known immunogenic macromolecules which may be used in the practice of the invention include, but are not limited to, polysaccharides, tRNA, nonmetabolizable synthetic polymers such as polyvinylamine, polymethacrylic acid, polyvinylpyrrolidone, mixed polycondensates (with relatively high molecular weight) of 4'4'-diaminodiphenyl-methane-3,3'-dicarboxylic acid and 4-nitro-2-aminobenzoic acid (See Sela, M., *Science* 166:1365–1374 (1969)) or glycolipids, lipids or carbohydrates. Preferably, the immunogenic carrier is a protein.

The animal immunized with the N-terminal segment of μCANP, either alone or as part of an immunogenic conjugate, may then be bled and the polyclonal sera isolated. See Vitto and Nixon, *J. Neurochem.* 47:1039–1051 (1986). Alternatively, monoclonal antibodies may be prepared according to the well known methods of Khöler and Milstein, *Nature* 256:495–497 (1975) where the spleen of the immunized animal is removed, and the cells fused with an immortal cell line to give hybridoma cells. Hybridomas secreting the desired antibodies may be obtained by subcloning of the hybridomas in HAT selection media and screening of the resultant clones for immunogenic activity with the 80-kDa isoform and lack of immunoreactivity with the 76-kDa and 78-kDa isoforms.

Most preferably, the N-terminal segment of μCANP is the first 21 amino acids having the following amino acid sequence [SEQ ID NO. 1]:

```
Ala Gly Ile Ala Ala Lys Leu Ala Lys Asp Arg Glu Ala Ala Glu Gly Leu
1               5                   10                  15

Gly Ser His Glu
            20
```

The antibodies employed in the practice of the present invention may be detectably labelled in a manner known per se. There are many different labels and methods of labeling known to those of ordinary skill in the art. Examples of the types of labels which can be used in the present invention include, but are not limited to, enzymes, radioisotopes, dyes, fluorescent compounds, chemiluminescent compounds, bioluminescent compounds and metal chelates. Those of ordinary skill in the art will know of other suitable labels for binding to the antibodies, or will be able to ascertain the same by the use of routine experimentation. The binding of these labels to the antibodies can be accomplished using standard techniques commonly known to those of ordinary skill in the art.

One of the ways in which the antibodies can be detectably labeled is by linking the same to an enzyme. This enzyme, in turn, when later exposed to its substrate, will react with the substrate in such a manner as to produce a chemical moiety which can be detected as, for example, by spectrophotometric, fluorometric or by visual means. Enzymes which can be used to detectably label antibodies include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase.

The antibodies may also be labeled with a radioactive isotope which can be determined by such means as the use of a gamma counter or a scintillation counter or by autoradiography. Isotopes which are particularly useful for the purpose of the present invention include: $^{3}$H, $^{125}$I, $^{131}$I, $^{32}$P, $^{35}$S, $^{14}$C or the radioisotopes of lead, mercury, thallium, technetium or indium ($^{203}$Pb, $^{198}$Hg, $^{201}$Tl, $^{99m}$Tc, $^{111}$In).

It is also possible to label the antibodies with a fluorescent compound. When the fluorescently labeled annexine is exposed to light of the proper wave length, its presence can then be detected due to the fluorescence of the dye. Among the most commonly used fluorescent labelling compounds are fluorescein isothiocyanate, rhodamine, phycoerythrin, phycocyanin, allophycocyanin, o-phthaldehyde and fluorescamine.

The antibodies can also be detectably labeled using fluorescent emitting metals such as $^{152}$Eu, or others of the lanthanide series. These metals can be attached to the antibodies using such metal chelating groups as diethylenetriaminepentaacetic acid (DTPA) or ethylenediaminetetraacetic acid (EDTA).

Labelling is also possible by means of a paramagnetic contrast agent which is detectable in a MRI (magnetic resonance imaging) system. It is possible to use gadolinium, cobalt, nickel, manganese or iron complexes by means of which conjugates may be provided as diagnostic agents which are detectable in a MRI system. A strong magnetic field is used in such systems in order to adjust the nuclear spin vectors of the atoms in the organism. Then the field is destroyed which causes the nuclei to return to their initial state. This process is observed and recorded.

The antibodies also can be detectably labeled by coupling them to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibodies. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Another technique which may also result in greater sensitivity when used in conjunction with the present invention consists of coupling the antibody to low molecular weight haptens. The haptens can then be specifically detected by means of a second reaction. For example, it is common to use such haptens as biotin (reacting with avidin) or dinitrophenyl, pyridoxal and fluorescamine (reacting with specific anti-hapten antibodies) in this manner. Amplification strategies may be readily applied to these and other labels.

The detectable antibodies are ideally suited for the preparation of a kit. Such a kit may comprise a carrier means being compartmentalized to receive in close confinement therein one or more container means such as vials, tubes and the like, each of said container means comprising the separate elements of the assay. For example, there may be a container means containing a detectable antibody specific for all isoforms of μCANP, and further container means containing, for example, standard serial dilutions of the 76-kDa, 78-kDa and 80-kDa isoforms of μCANP in solution. The detectable antibody may be detectably labelled. A further container means may contain a means for carrying out an electrophoretic separation of the 76-kDa, 78-kDa and 80-kDa isoforms of μCANP. The standard solutions of μCANP may be used as standards for the electrophoretic separation of the μCANP isoforms of a tissue sample and to prepare standard curves with the concentration of the 76-kDa, 78-kDa and 80-kDa isoforms of μCANP plotted on the abscissa and the detection signal on the ordinate. The results obtained from the supernatant of a tissue sample such as brain cells or fibroblasts may be interpolated from such a plot to give the concentration of the 76-kDa, 78-kDa and 80-kDa isoforms of μCANP and, thus, an indication of whether the individual has Alzheimer's disease. Further container means may comprise a detectably labelled antibody that is immunoreactive with the detectable antibody that is specific for the active 76-kDa isoform of μCANP and the 80-kDa isoform of μCANP.

Alternatively, the kit may comprise a carrier means being compartmentalized to receive in close confinement therein a container means containing a first detectable antibody specific for only the 80-kDa isoform of μCANP and a second detectable antibody which is specific for all isoforms of μCANP. In a preferred embodiment, the first and second detectable antibodies are labelled with different labels which can be discriminated by different detection methods. Further container means may contain standard serial dilutions of the 76-kDa, 78-kDa and 80-kDa isoforms of μCANP in solution.

Alternatively, the kit may comprise a carrier means being compartmentalized to receive in close confinement therein a container means containing a first detectable antibody specific for only the 80-kDa isoform of μCANP and a second detectable antibody which is specific for the 76-kDa isoform of μCANP. In a preferred embodiment, the first and second detectable antibodies are labelled with different labels which can be discriminated by different detection methods. Further container means may contain standard serial dilutions of the 76-kDa and 80-kDa isoforms of μCANP in solution.

The means for separating/identifying the μCANP isoforms may include slab gels that can be used to electrophoretically separate the μCANP isoforms. Preferably, such slab gels are sodium dodecyl sulfate (SDS)-polyacrylamide gels.

In carrying out the method for detecting the isoforms of μCANP, the specific concentrations of the isoforms, the temperature and time of incubation, as well as other assay conditions may be varied, depending on various factors including the concentration of the μCANP isoforms, the nature of the sample, and the like. Those skilled in the art will be able to determine operative and optimal assay conditions by employing routine experimentation.

Detection of the detectable antibodies and, thus, the isoforms of μCANP, may be accomplished with a scintillation counter if, for example, the detectable antibodies are labelled with a radioactive gamma emitter, or by a fluorometer if the detectable label is a fluorescence emitter. In the case of an enzyme label, the detection can be accomplished by colorimetric methods which employ a substrate for the enzyme. Detection may be accomplished by comparison with the isoform standards.

Where first and second antibodies, as described herein, are employed to determine the relative ratio of the 76-kDa/80-kDa isoforms, the two antibodies may be detectably labelled with two different labels with may be separately detected. In this embodiment, the ratio may be obtained from a single incubation with both antibodies. The sample comprising the μCANP isoforms may be immobilized to a solid phase carrier such as nitrocellulose or polyvinylidene difluoride membrane (Immobilon-P), contacted with the first and second detectably labelled antibodies, and the amount of bound label determined. Other steps such as washing, stirring, shaking, filtering and the like may be added to the assay as is customary or necessary for the particular situation.

As described in more detail below, there is evidence that the activation of μCANP leads to the development of neurofibrillary pathology and β-amyloid formation which are hallmarks of Alzheimer's disease. Thus, agents which inhibit the activation of μCANP may be useful in treating or preventing the neuropathology characteristic of Alzheimer's disease. Thus, the invention also relates to a method for screening a drug for use in the treatment or prevention of Alzheimer's disease, comprising (a) obtaining a first animal brain sample, preferably a cortical brain slice;

(b) determining the relative ratio of the active 76-kDa isoform of μCANP to the 80 kDa isoform in the first animal brain sample;

(c) incubating a second animal brain sample with an aqueous solution of $Ca^{++}$ and a drug suspected of being useful in treating or preventing Alzheimer's disease;

(d) determining the relative ratio of the active 76-kDa isoform of μCANP to the 80 kDa isoform in the tissue sample obtained in step (c);

wherein when the 76-kDa/80-kDa ratio of the animal brain sample contacted with said drug as determined in step (d) is reduced compared to the 76-kDa/80-kDa ratio obtained in step (b) confirms that the drug is useful for treating or preventing Alzheimer's disease.

Preferably, the first and second tissue samples are obtained premortem from the brain of an animal or postmortem from an individual having Alzheimer's disease.

Alternatively, the invention relates to a method for screening a drug for use in the treatment or prevention of Alzheimer's disease, comprising (a) obtaining a first fibroblast sample from an animal;

(b) determining the relative ratio of the active 76-kDa isoform of μCANP to the 80 kDa isoform in the first fibroblast sample;

(c) incubating a second fibroblast sample with an aqueous solution of $Ca^{++}$, a calcium ionophore, and a drug suspected of being useful in treating or preventing Alzheimer's disease;

(d) determining the relative ratio of the active 76-kDa isoform of μCANP to the 80 kDa isoform in the fibroblast sample obtained in step (c);

wherein when the 76-kDa/80-kDa ratio of the fibroblast sample contacted with said drug as determined in step (d) is reduced compared to the 76-kDa/80-kDa ratio obtained in step (b) confirms that the drug is useful for treating or preventing Alzheimer's disease.

In step (b) of either method, the tissue sample may be first homogenized in a buffer and centrifuged to give a supernatant and then the relative ratio of the active 76-kDa isoform of μCANP to the 80-kDa isoform in the supernatant is then determined. The relative ratio of the active 76-kDa isoform of μCANP to the 80-kDa isoform may be determined by (e) separating the isoforms of μCANP in the supernatant by gel electrophoresis, (f) contacting the separated 76-kDa isoform of μCANP and the 80-kDa isoform of μCANP with at least one detectable antibody which is immunoreactive therewith, (g) detecting the amount of detectable antibody bound to the 76-kDa and the 80-kDa isoforms of μCANP to give a relative signal for each isoform, and (h) dividing the relative signal corresponding to the 76-kDa isoform by the relative signal corresponding to the 80-kDa isoform to give said ratio.

Alternatively, the relative ratio of the active 76-kDa isoform of μCANP to the 80-kDa isoform may be determined by (e) contacting the supernatant with a first and a second detectable antibody, wherein the first detectable antibody is immunoreactive only with the 80-kDa isoform of μCANP and the second detectable antibody is immunoreactive with the 76-kDa, 78-kDa and 80-kDa isoforms of μCANP;

(f) detecting the amount of detectable first and second antibodies bound to the respective isoforms of μCANP to give a relative signal; and (g) dividing the relative signal corresponding to the 76-kDa, 78-kDa and 80-kDa isoforms by the relative signal corresponding to the 80-kDa isoform to give said ratio.

The conversion of the 80-kDa isoform to the 76-kDa isoform is calcium dependent. Thus, in step (c), the tissue sample is first incubated with calcium and the drug for a time sufficient to alter the 76-kDa/80-kDa ratio. Typically, the drug and calcium are contacted with the tissue sample for about 5 to about 60 min. The concentration of calcium may range from 0–5 mM. The concentration of the drug may range from 0.001 to about 1000 μM. Preferably, the tissue sample is first incubated with the drug at about 4° C. and is then incubated at about 30° C. with calcium and the drug. When fibroblasts are employed, a calcium ionophore such as A23187 is employed at a concentration range of 1–100 μM. The tissue sample is then homogenized in a buffer and centrifuged to give a supernatant, and then the relative ratio of the active 76-kDa isoform of μCANP to the 80-kDa isoform in said supernatant is determined.

Figure 1B:
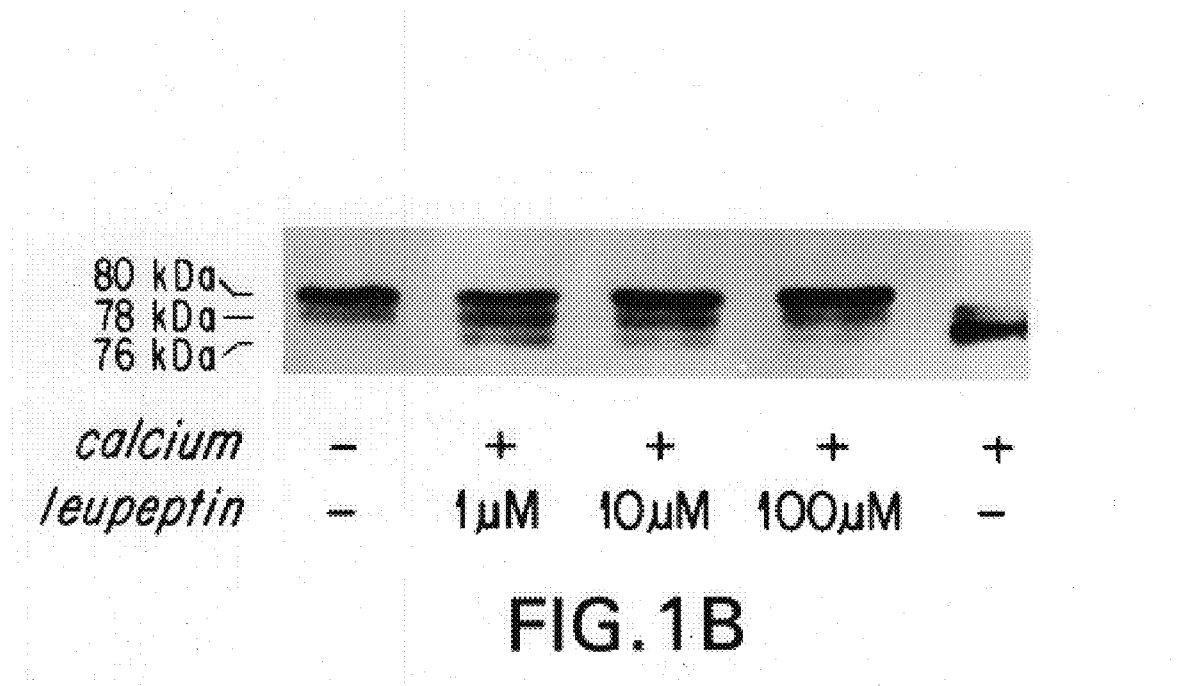
FIG. 1(B) depicts a gel electrophoresis showing the autolysis of μCANP from human erythrocytes in vitro.
Figure 2:
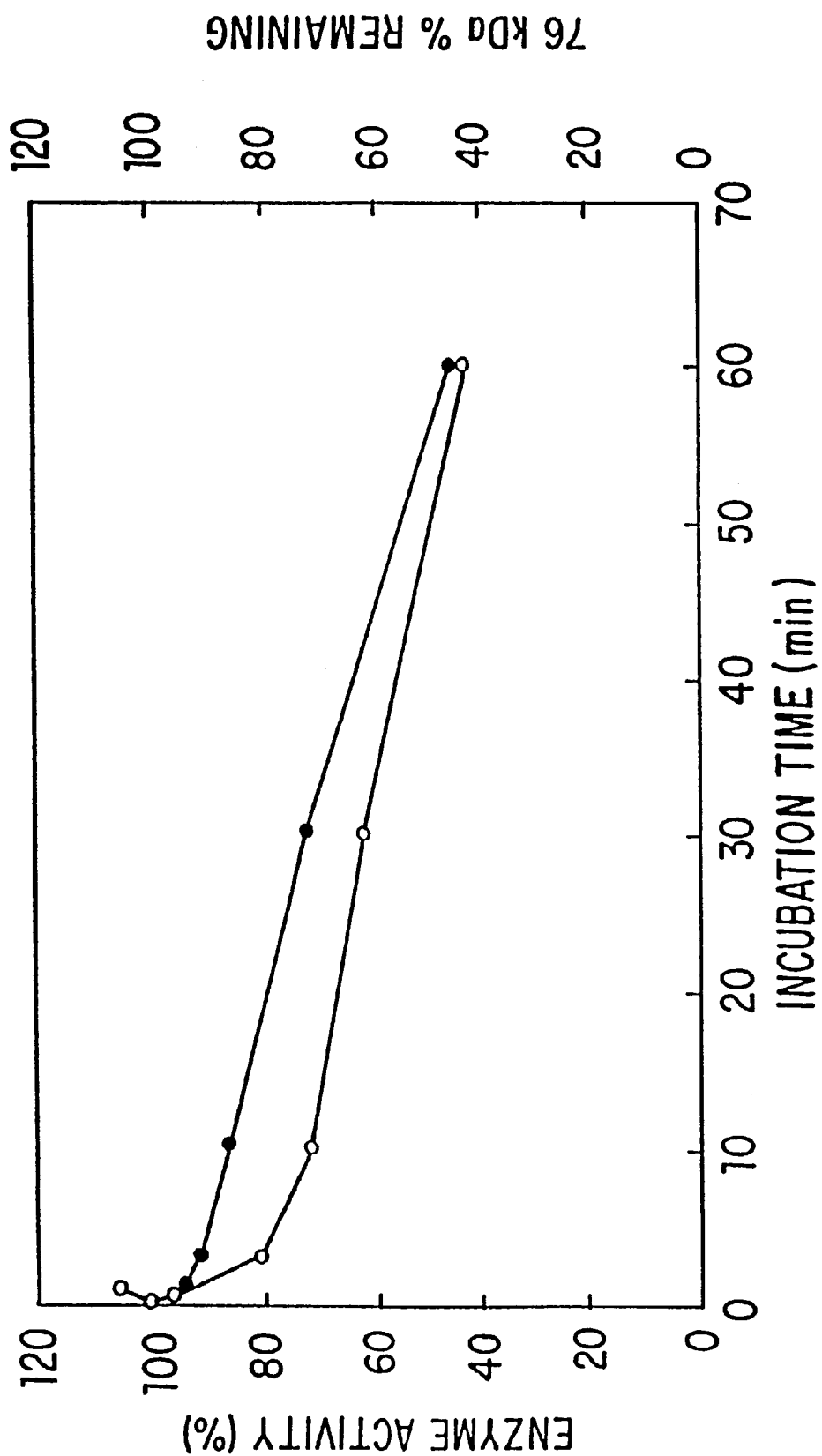
FIG. 2 depicts a graph showing the relationship between enzyme activity and μCANP content.
Figure 3:
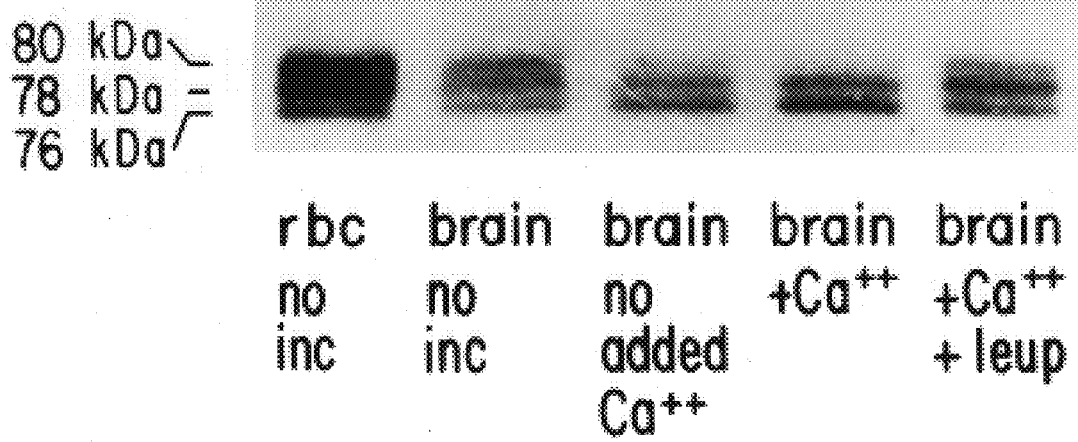
FIG. 3 depicts an immunoblot analysis of μCANP autolysis in human brain slices (prefrontal cortex).

In the practice of the invention, a monoclonal antibody raised against human μCANP (Samis, J. A., et al., *Biochem. J.* 246:481–488 (1987); and Elce, J. S., et al., *Biochem. J.* 261:1039–1042 (1989), the contents of which are fully incorporated by reference herein) may be used to detect by Western blot analysis the three isoforms of the catalytic subunit of μCANP in human brain extracts. These isoenzymes exhibit molecular masses on SDS polyacrylamide gels of 80 kDa, 78 kDa and 76 kDa identical to those in human erythrocytes (Samis, J. A., et al., *Biochem. J.* 246:481–488 (1987); Elce, J. S., et al., *Biochem. J.* 261:1039–1042 (1989); Samis et al., *Biochem. J.* 246:481–487 (1987)) (FIG. 1a). When human erythrocyte μCANP was activated in vitro by adding calcium, hydrolysis of purified spectrin by the enzyme was accompanied by N-terminal cleavage of the 80-kDa isoform at the $GLY_{26}$-$LEU_{27}$ peptide bond and formation of the 76-kDa isoform (The 76-kDa isoform of μCANP, generated by autolysis, separated by SDS-PAGE and transferred to DF-immobilon membranes, was subjected to N-terminal analysis by the Edman degradation method at the Harvard University Microchemistry Facility, courtesy of William Lane.) (FIG. 1b). Conversion of the 80-kDa μCANP isoform to 78-kDa and 76-kDa isoforms was nearly complete within 30 sec. Enzyme activity was preserved in the absence of 80-kDa μCANP and remained proportional to the amount of 76-kDa isoform, confirming other recent data that the 76-kDa isoform is enzymatically active (Pontremoli, S., et al., *Biochem. Biophys. Res. Commun.* 123(1):331–337 (1984); Inomata, M., et al., *Biochem. Biophys. Res. Commun.* 138(2):638–643 (1986)) (FIG. 2). Although human brain μCANP is unstable in cell free extracts, conversion of the 80-kDa isoform of μCANP to the 76-kDa isoform could be demonstrated in slices of human neo-cortex incubated with calcium (FIG. 3). Autolysis of μCANP was confirmed by demonstrating loss of the extreme N-terminus of the 80-kDa isoform using a polyclonal antibody raised against the first 21 amino acids of the polypeptide (A 34-mer synthetic peptide corresponding to the extreme N-terminal amino acid sequence of μCANP deduced from a human liver cDNA (Imajoh et al., *Biochem.* 27:8122 (1988), the contents of which are fully incorporated by reference herein) was used unconjugated to immunize 2-month-old New Zealand rabbits as described previously (Vitto & Nixon, *J. Neurochem.* 47:1039–1051 (1986)). The amino acid sequence of this 34-mer is as follows [SEQ. ID NO. 2]:

```
Ser Glu Glu Ile Ile Thr Pro Val Tyr Cys Thr Gly Val Ser Ala Gln Val Gln
1               5                   10                  15

Lys Gln Arg Ala Arg Glu Leu Gly Leu Gly Arg His Glu Asn Ala Ile
        20                  25                  30
```

Antiserum prepared against this 34-mer specifically cross-reacted with the 80-kDa isoform of μCANP on Western blot analyses of 30,000 xg supernatant extract from human brain.

To evaluate the relative state of μCANP activation in the brain in Alzheimer disease, the three μCANP isoforms were quantitated by immunoassay of extracts of brain tissue from 22 individuals who had premortem diagnoses of dementia and met neuropathological criteria for Alzheimer disease, and 17 individuals who were free of clinical neurologic disease (Khachaturian, Z. S., *Arch. Neurol.* 42:1097–1105 (1985)) and neuropathological evidence (Mirra, S. S., et al., *Neurology* 41:479–486 (1991)) for Alzheimer disease. The Alzheimer and control groups were matched with respect to age of the individual (75.8±2.0 years vs. 68.9±2.6 years, respectively), and postmortem interval for brain samples (12.2±1.3 hr vs. 12.0±1.8 hr, respectively).

The content of cytosolic 80-kDa μCANP was substantially lower in the Alzheimer group than in controls (22.7±1.5% vs. 37.2±2.2%, p<0.001, unpaired t-test). By contrast, autolytically activated (76 kDa) μCANP was increased nearly two-fold in Alzheimer brain (41.2±1.6%) than in controls (26.6±2.2%) (p<0.001). The 78-kDa μCANP isoform, was unchanged. The ratio of 76-kDa to 80-kDa μCANP for individual brain samples was nearly 3-fold higher in the Alzheimer group (2.20±0.39 vs. 0.81±0.10). The sum of the three μCANP isoforms was not changed (Table 1).

TABLE 1

μCANP Content (μg/mg protein)

| | Prefrontal Cortex | Putamen | Cerebellum |
|---|---|---|---|
| Control | 5.67 ± 0.41 (17) | 6.61 ± 0.53 (8) | 5.89 ± 0.43 (14) |
| Alzheimer's disease | 5.36 ± 0.29 (22) | 5.98 ± 0.33 (21) | 5.74 ± 0.49 (21) |
| Huntington's disease | 5.97 ± 0.46 (12) | 5.95 ± 0.47 (14) | 5.90 ± 0.43 (16) |

Table 1. μCANP content in brain regions from control individual and patients with Alzheimer disease (AD) and Huntington disease, measured by immunoassay as previously described (Takeuchi, K. S., et al., J. Neurochem. 92:526–532 (1992)). μCANP was partially purified by DEAE-cellulose chromatography from 0.5 g brain samples as described in Example 1. Total μCANP content was quantified densitometrically after SDS-polyacrylamide gel electrophoresis and immunoblot analysis. The weight of μCANP on the immunoblot was calculated from standard curves prepared by measuring the immunostaining intensity of varying known amounts of human erythrocyte μCANP on immunoblots. Standard amounts of μCANP were analyzed on every immunoblot that contained brain samples to control for possible minor variations in the immunostaining methods. Results are means ± S.E.M. of the numbers shown in parentheses.

The abnormal ratio of μCANP isoforms in the cytosolic fraction did not reflect a shift in their cellular distribution (Table 2). About 30% of the total μCANP was associated with the particulate fraction in both control and Alzheimer groups (Table 2). The higher proportion of 76-kDa μCANP observed in this fraction is consistent with the hypothesis that μCANP is activated mainly on the membrane (Inomata, M., et al., *J. Biol. Chem.* 264(31):18838–18843 (1969); Pontremoli, S., et al., *Biochem. Biophys. Res. Commun.* 128(I):331–338 (1985)). Interestingly, the 76-kDa to 80-kDa isoform ratios in the cytosolic fractions from control brains correlated significantly with those in corresponding particulate fractions of control brains (r=0.839, p<0.005), but this relationship was disturbed in Alzheimer brain (r=0.077).

TABLE 2

| | Control (N = 8) | AD (N = 9) |
|---|---|---|
| Cytosolic Fraction | | |
| μCANP content, μg/mg protein | 1.52 ± 0.15 (69.7 ± 3.9)# | 1.60 ± 0.12 (73.0 ± 3.3) |
| Isoform content, % of total | | |
| 80 kDa | 31.3 ± 2.0 | 24.4 ± 1.4** |
| 78 kDa | 38.0 ± 0.8 | 36.4 ± 1.3 |
| 76 kDa | 30.7 ± 2.5 | 39.2 ± 2.6* |
| Membrane Fraction | | |
| μCANP content, μg/mg protein | 0.65 ± 0.08 (30.3 ± 3.9) | 0.59 ± 0.07 (27.0 ± 3.3) |
| Isoform content, % of total | | |
| 80 kDa | 18.2 ± 1.3*** | 17.5 ± 1.3***,**** |
| 78 kDa | 41.5 ± 1.3* | 39.4 ± 1.0 |
| 76 kDa | 40.4 ± 1.8*** | 43.1 ± 1.7*** |

Table 2. Subcellular distribution of μCANP isoforms in the prefrontal cortex of control and Alzheimer patients. Brain tissue homogenate was centrifuged at 15,000 × g for 30 min. at 4° C. to obtain a cytosolic (supernatant) fraction and membrane (pellet) fraction. μCANP content in these fractions was quantified by immunoassay as described above in the legend for Table 1. Data are expressed as mean ± S.E.M. Numbers in parentheses are mean percentages of the total (cytosolic + membrane fraction ) (μCANP content ± S.E.M., *p < 0.05;  p < 0.01; *p < 0.005 vs. control cytosolic μCANP isoform; ****p < 0.005 vs. AD cytosolic μCANP.

Figure 4:
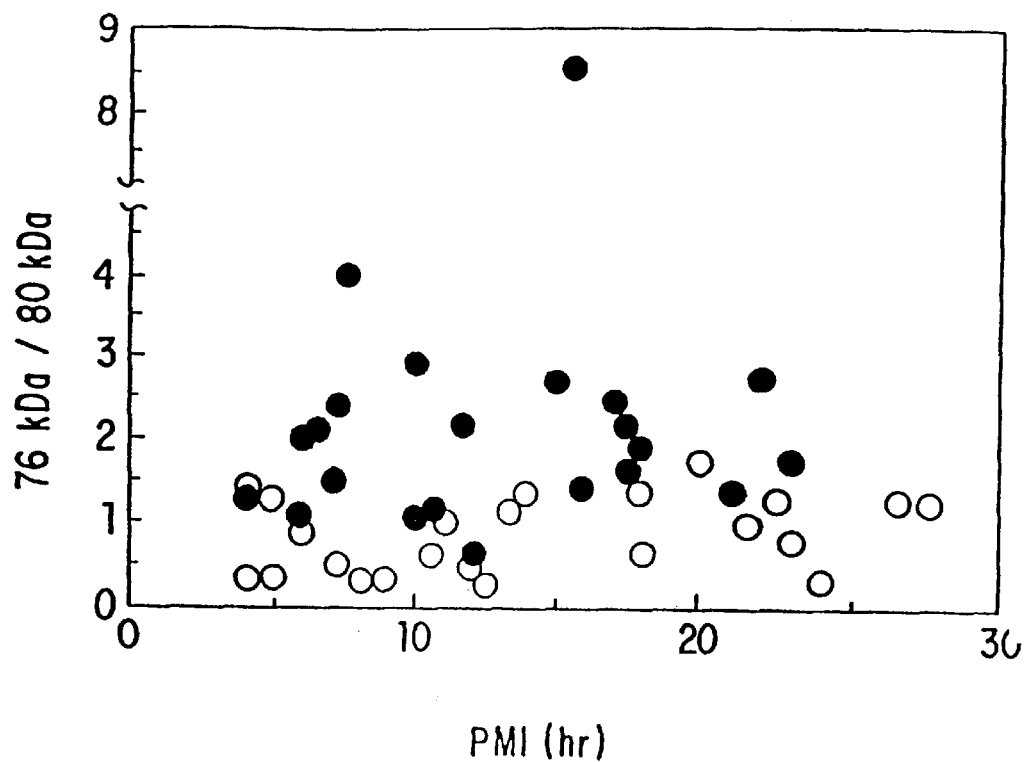
FIG. 4 depicts a graph showing the ratio of 76 kDa/80 kDa isoforms of μCANP in prefrontal cortex from control individuals (O) and AD patients (●), plotted against postmortem interval (PMI).

The degree of abnormal μCANP activation was comparable in Alzheimer brains at all postmortem intervals. The ratio of 76 kDa to 80 kDa isoforms regressed against postmortem interval yielded non-significant correlations in control (r=0.355), Alzheimer (r=0.155), or combined groups (r=0.148) (FIG. 4). The possibility cannot be excluded, however, that isoform ratios change significantly within the first few hours after death. The degree of μCANP activation also did not significantly correlate with age within the range studied for any group.

Because some neurons are degenerating in Alzheimer neocortex, the degree of μCANP activation in two brain areas was examined where neuronal degeneration is reported to be minimal or absent (Pro, J. D., et al., *Neurology* 30:820–825 (1980); Katzman & Terry, in *The Neurobiology of Aging*, Katzman & Terry, eds., F. A. Davis Co., New York, pp. 51–84 (1983)). The ratio of 76-kDa to 80-kDa μCANP isoforms was significantly elevated in both putamen (46%, p<0.005) and cerebellum (58%, p<0.005) in the Alzheimer cases FIGS. 5(A and C). By contrast, the proportions of μCANP isoforms were normal in the prefrontal cortex and cerebellum from patients with Stage III Huntington disease (FIGS. 5(A and C). Consistent with evidence that ongoing neuronal degeneration is associated with CANP activation (Dure, L. S., et al., *Ann. Neurol.* 30:785–793 (1991)), μCANP activation was increased 50% (p<0.05) in samples of putamen from Huntington patients (HD) (Vonsattel, J. -P., et al., *J. Neuropathol. Exp. Neurol.* 44:559–577 (1985); Roos, R. A. C., et al., *J. Neurol. Neurosurg. Psychiatry* 48:422–425 (1985)), where neuronal cell loss is considerable (FIG. 5B).

The modestly increased μCANP activation seen in Huntington putamen could possibly be explained by influx of calcium associated with either end-stage cell death occurring in this region or NMDA receptor stimulation, which is believed to be an underlying mechanism of neuronal cell death in Huntington's disease (Dure, L. S., et al., *Ann. Neurol.* 30:785–793 (1991)). The much higher levels of μCANP activation in Alzheimer neocortex and the similar abnormalities in brain regions exhibiting minimal neuronal degeneration indicate that μCANP activation is not a consequence simply of end-stage neuronal degeneration but reflects a more widespread metabolic alteration that precedes and possibly contributes to neuronal degeneration. In this regard, the extensive loss of synapses in neocortex, which correlates with dementia (Terry et al., *Ann. Neurol.* 30:572–580 (1991); Hamos et al., *Ann. Neurol.* 39: 355 (1991); Dekosky & Scheff, *Ann. Neurol.* 27:457–464 (1990)) is relevant since μCANP is enriched at synapses (Peterson, C., et al., *Neurosci. Lett.* 121:239–243 (1991)) and activation of CANP at nerve terminals has been associated with terminal degeneration (Swanson & Vrbóva, *Devel. Brain Res.* 33:199–203 (1987); O'Brien, R. A. D., et al., *Neuroscience* 12:637–646 (1984)).

Widespread μCANP activation in brain is consistent with evidence in fibroblasts of Alzheimer patients for increased degradation of spectrin (Peterson, C., et al., *Neurosci. Lett.* 121:239–243 (1991)) and diminished content of protein kinase C (Saitoh, T., et al., *Lab. Invest.* 64:596–616 (1991)) which are two preferred substrates of CANPs. Brain spectrin breakdown is also increased in cortex and hippocampus of Alzheimer brain (Masliah, E., et al., *Brain Res.* 531:36–44 (1990)). Previous reports that total CANP activity is not significantly altered in Alzheimer brain (Kawashima, S., et al., *Biomed. Res.* 10(1):17–23 (1989); Mantle & Perry, *J. Neurol. Sci.* 102:220–224 (1991); Nilsson, E., et al., *Neurobiol. Aging* 11:425–431 (1990)) accord with our results and suggest that measurements of the total CANP pool may not sensitively reflect functional activity of the CANP system.

Apart from contributing to synaptic loss and cell death, abnormal μCANP activation may have additional consequences in neurons that bear on the development of neurofibrillary pathology and β-amyloid formation. These include the abnormal processing of cytoskeletal proteins and other sensitive CANP substrates, which include the amyloid precursor protein (APP) (Siman et al., in *Neurotoxicity of Excitatory Amino Acids*, A. Guidotti, Ed. (Raven Press, New York, 1990), pp. 145–161; Lee et al., *Proc. Natl. Acad. Sci. USA* 88:7233–7347 (1991) and alterations of the activities of calcium-dependent protein kinases and phosphatases (Togari, A., et al., *Biochem. Biophys. Res. Commun.* 134(2): 749–754 (1968); Kishimoto, A., et al., *J. Biol. Chem.* 258:1156–1164 (1983); Tallant, E. A., et al., *Biochem.* 27:2205–2211 (1988); Nixon, R. A., *Ann. N.Y. Acad. Sci.* 568:198–208 (1989)) which may in turn also affect APP processing or secretion. In this regard, reduced levels of soluble (secreted) forms of APP have been found in the cerebrospinal fluid of Alzheimer patients. In preliminary studies, the degree of μCANP activation in the neocortex of Alzheimer patients exhibited a highly significant inverse correlation with the level of soluble APP in human brain. These results are compatible with the hypothesis that β-amyloid or APP fragments have a primary role in Alzheimer-related neurodegeneration. The toxicity of β-amyloid or APP fragments may, in part, be mediated through alterations in calcium homeostasis, which would be expected to lead to CANP activation.

Pharmacological modulation of the CANP system, which is effective in vivo in limiting neural damage in ischemia and vasospasm (Siman, R., in *Neurotoxcity of Excitatory Amino Acids*, A. Guidotti, ed., Raven Press, New York, pp. 145–161 (1990); Lee, K. S., et al., *Proc. Natl. Acad. Sci. USA* 88:7233–7347 (1991); Minami, N., et al., *J. Neurosurg.* 76:111–118 (1992)), merits further consideration as a potential therapeutic strategy in Alzheimer disease.

The following examples are illustrative, but not limiting, of the method and compositions of the present invention. Other suitable modifications and adaptations of the variety of conditions and parameters normally encountered in immunodiagnostics which are obvious to those skilled in the art are within the spirit and scope of the present invention.

EXAMPLES

Example 1

Immunoblot Analysis of μCANP in Prefrontal Cortex

FIG. 1(A) depicts the immunoblot analysis of μCANP in prefrontal cortex from two control (CONT) and two Alzheimer (AD) patients. Prefrontal cortex (0.5 g) from control or AD patients was homogenized with 10 vol. of 20 mM Tris HCl, pH 7.4, containing 2 mM EGTA, 1 mM EDTA, 1 mM benzamidine, 1 mM dithiothreitol, 1 mM phenylmethylsulfonyl fluoride (PMSF) and 0.32M sucrose (Buffer A). The homogenate was centrifuged at 15,000×g for 30 min at 4° C. and the supernatant was applied to a column (1.0×15 cm) of DEAE-cellulose (DE-52, Whatman) equilibrated with Buffer A. The column, extensively washed with Buffer A, was eluted with stepwise increments of KCl from 0 to 3 mM. μCANP was eluted from the column by 0.15M KCl in Buffer A. These fractions were subjected to 7.5% SDS-PAGE according to the method of Laemmli, *Nature* 227:680–685 (1970). Electroblotting was performed according to Towbin et al., *Proc. Natl. Acad. Sci. USA* 76:4350–4354 (1979), in a transfer buffer containing 15% methanol, 25 mM Tris and 192 mM glycine, pH 8.3. Proteins were transferred Electrophetically onto PVDF-membrane (Immobilon-P, Millipore) by applying 0.5 A of constant current for 2.5 h at 4° C. The blots were incubated with 5% nonfat dry milk solution containing 2 mM EGTA, 0.15M NaCl in 50 mM Tris-HCl, pH 7.4 (blocking buffer) for 1 h at room temperature. Immunoblot analysis was carried out with a rabbit monoclonal anti-μCANP antibody using peroxidase-conjugated goat anti-rabbit immunoglobulin G for 5 h at 4° C. After several washes of the blots with 50 mM Tris-HCl, pH 7.5, 0.15M NaCl, peroxidase activity was visualized with $H_2O_2$, 4-chloro-1-naphthol and N,N'-dimethyl-p-phenylenediamine. FIG. 1(A) shows μCANP in prefrontal cortex of two representative control brains (lanes 1, 2) and two AD brains (lanes 3, 4).

Example 2

Immunoblot Analysis of the Autolysis Products of μCANP

FIG. 1(B) depicts the immunoblot analysis of the autolysis products of μCANP from human erythrocytes in vitro. Human erythrocyte μCANP was purified from normal adult blood as described before (Inomata, M., et al., *J. Biochem.* 93:291–294 (1983); Fairbanks, G., et al., *Biochemistry* 10(13):2606 (1971)) (lane 1); incubation with 5.3 mM $CaCl_2$ (final free calcium concentration was 50 μM) and 2.2 μg of human erythrocyte spectrin (Bennet, V., et al., *Nature* 299:126 (1982)) for 30 sec at 30° C. in the presence of either 1 μM leupeptin (lane 2), 10 μM leupeptin (lane 3), or 100 μM leupeptin (lane 4), or incubation with 5.3 mM $CaCl_2$ and 2.2 μg of spectrin for 30 sec at 30° C. (lane 5).

FIG. 2 shows the relationship between enzyme activity and μCANP content. After preincubation of human erythrocyte μCANP with calcium and spectrin, 1 mM EGTA was added to stop the reaction. Half of each sample was applied to SDS/PAGE and immunoreactivity of each μCANP isoform was quantified using a Bio-Rad Video Densitometer Model 620. The other half was used to measure enzyme activity as previously described (Takeuchi, K. S., et al., *J. Neurochem.* 92:526–532 (1992)) by adding [$^{14}C$]azocacein as substrate and 4 mM $CaCl_2$ (final free calcium concentration was 125 μM). Note that the 78 kDa isoform completely disappears by 1 min of incubation. ○: protease activity. ●: μCANP 76 kDa content.

FIG. 3 shows μCANP autolysis in human brain slices. Sections of fresh postmortem human brain (prefrontal cortex) (200 μM) were incubated at 37° C. for 60 min with Buffer A with or without $CaCl_2$ (final concentration 5 mM). Slices were then rinsed with Buffer A (1 ml×2), homogenized, and centrifuged 15,000×g for 30 min at 4° C. The supernatant was subjected to immunoblot analysis as described above. Human erythrocyte μCANP (lane 1); human brain μCANP from unincubated slices (lane 2) or slices incubated in the absence of exogenous calcium (lane 3), 5 mM $CaCl_2$ (lane 4), or with 5 mM $CaCl_2$ plus 10 μM leupeptin (lane 5).

Example 3

Comparison of Control with Alzheimer's Diseased Brains

FIG. 4 depicts a graph showing the ratio of 76 kDa/80 kDa isoforms of μCANP in prefrontal cortex from control individuals (○) and AD patients (●), plotted against postmortem interval (PMI). Immunoassay of individual isoforms (FIG. 1) was performed as described in the legend to Table 1.

Example 4

Figure 5A:
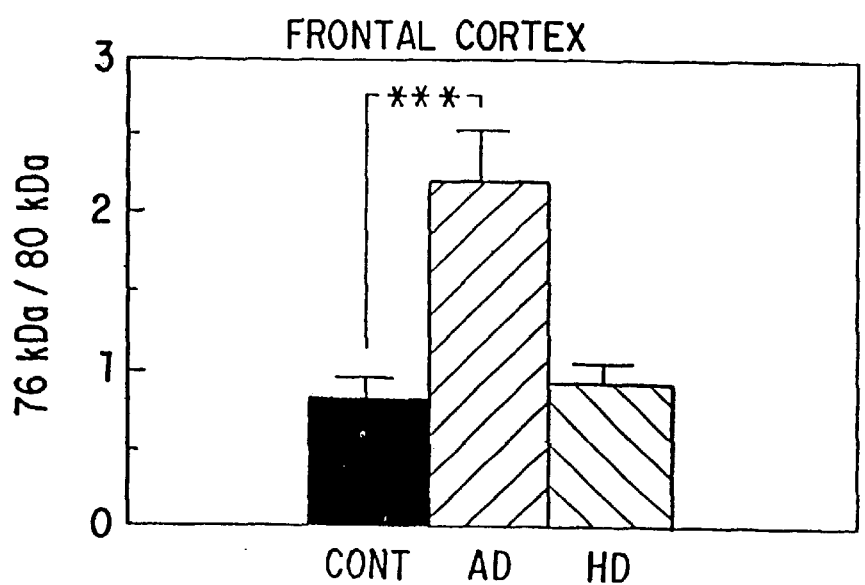
(FIG. 5A) Prefrontal cortex.
Figure 5B:
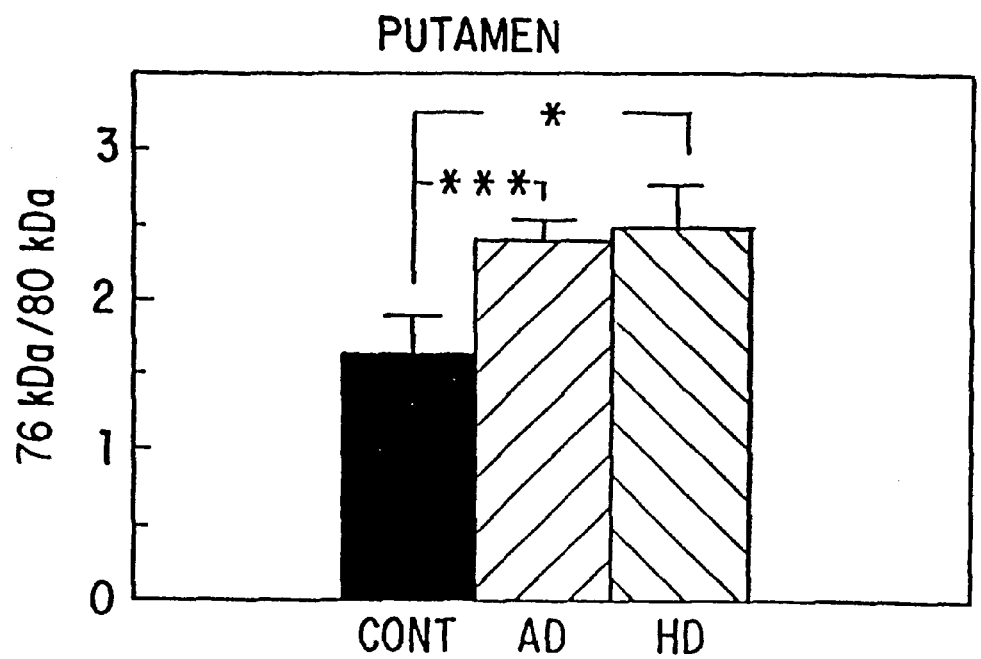
(FIG. 5B) Putamen.
Figure 5C:
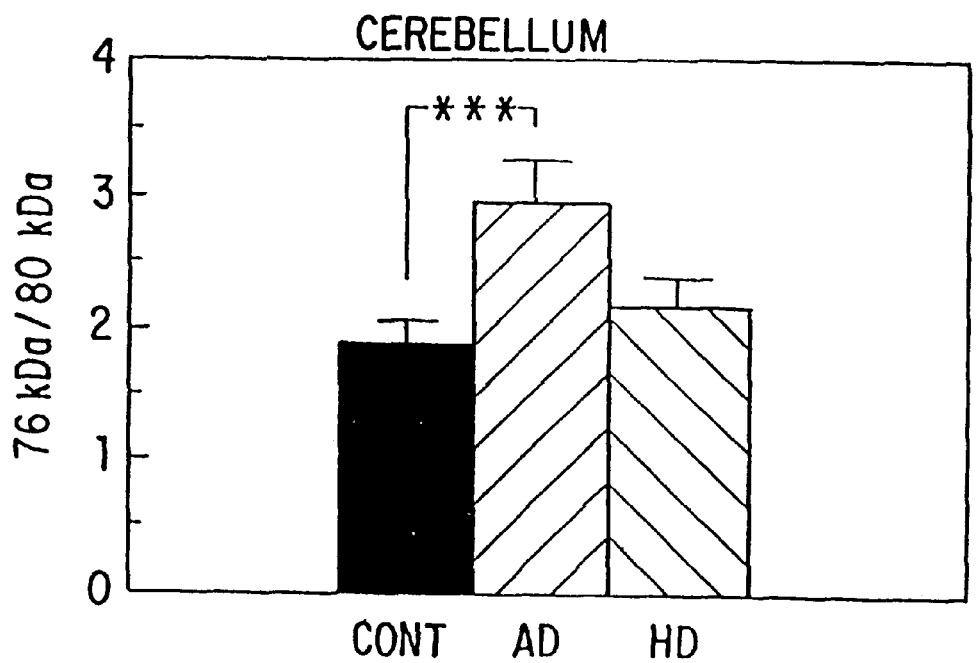
(FIG. 5C) Cerebellum.

Comparison of Isoform Levels in Alzheimer's Disease Brain and Huntington's Disease Brain FIGS. 5(A–C) depict the μCANP isoform ratios (76 kDa/80 kDa) in brain regions from control, Alzheimer and Huntington disease (HD) brains measured by Western blot immunoassay as described in Example 3. (FIG. 5A) Prefrontal cortex: mean values±S.E.M. for PMI and age from HD (n=12), control (n=17), AD cases (n=22) were 10.5±1.9 hr and 54.6±3.3 years. ***$p<0.005$. (FIG. 5B) Putamen: The mean values±S.E.M. of PMI and age were 10.6±2.9 hr and 68.5±1.9 years, 14.8±1.4 hr and 71.8±2.3 years, or 14.1±2.0 hr and 60.1±2.6 years in control (n=8), AD (n=21) or HD (n=14) patients, respectively. *$p<0.05$, *$p<0.05$. (FIG. 5C) Cerebellum: The mean±S.E.M. of PMI and age were 7.6±1.6 hr and 67.8±4.2 years, 13.1±1.7 hr and 76.0±1.9 years, or 10.6±2.1 hr and 54.6±3.1 years in control (n=14), AD (n=21) or HD (n=16) patients, respectively. *$p<0.005$.

Example 5

Abnormalities in calpain regulation in Alzheimer's disease—Fibroblast studies

Methods

Figures 6A, 6B:
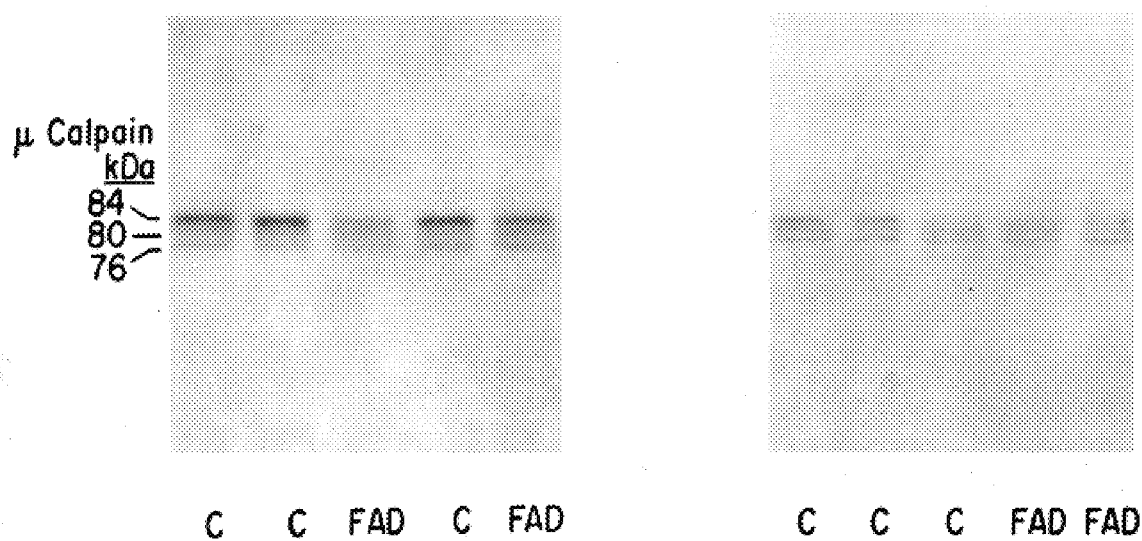
FIGS. 6(A and B) depict immunoblot analysis of fibroblasts from control and affected individuals from the Canadian FAD cohort. The figure shows that the ratio of activated calpain isoform (76 kDa) to latent isoform (84 kDa) is elevated in fibroblasts from phenotypically-affected individuals of the FAD Cohort (C=control).

Experiments using fibroblasts from. FAD cohorts were carried out in collaboration with Dr. Jesse Sisken (University of Kentucky Medical School), who provided fibroblast samples from control (C) and AD-affected individuals. Stocks were maintained in DMEM (Gibco) supplemented with 15% FBS (Sigma). Cells were set up on Corning 100-mm culture plates in DMEM (Gibco) supplemented with 17% FBS (Gibco). After 1–2 days, the cultures were considered "subconfluent" and were harvested. The cells were gently scraped off the surface with a sterile rubber policeman. The cells were then transferred to a centrifuge tube, centrifuged, and the cell pellet was resuspended in medium with FBS, transferred to a cryovial, recentrifuged and frozen. Alternatively, cells were harvested by addition of 0.05% trypsin-EDTA, neutralization by medium with FBS. Immunoassay of the individual isoforms was performed as described in the legend to Table 1. The results are depicted in FIGS. 6 (A and B).

Results

In collaboration with Dr. Jesse Sisken (University of Kentucky Medical School), studies of the calpain system were initiated in cultured fibroblasts from individuals from a large familial Alzheimer disease cohort, in which Alzheimer disease is expressed early and in which the gene defect has been localized to chromosome 21 (but is not at the APP locus) (Nee et al., *Arch. Neurol.* 40:203–208 (1984); Tanzi et al., *Science* 235:880–884 (1987); Tanzi et al., *Nature* 329:156–157 (1987); Tanzi et al., *Nature* 331:528–530 (1988)). Studies to date on 7 controls and 6 phenotypically affected individuals (two experiments are shown in FIGS. 6(A and B), have identified an abnormally high ratio of the activated μcalpain isoform (76 kDa) to the latent (84 kDa) μcalpain isoform in the AD cases ($p<0.02$, paired t test). The demonstration of the same type of μcalpain abnormality in fibroblasts as seen in postmortem human brain, supports the idea that this abnormality is widespread in AD and is not related solely to end-stage cell death phenomena. Thus, fibroblast cells are useful models for investigating calpain system activation in relation to downstream effects on kinases, APP metabolism and other AD-related processes.

Having now fully described this invention, it will be understood to those of ordinary skill in the art that the same can be performed within a wide and equivalent range of conditions, formulations and other perimeters without affecting the scope of the invention or any embodiment thereof. All patents and publications cited herein are fully incorporated by reference herein in their entirety.

What is claimed is:

1. A kit which is useful for detecting Alzheimer's disease in an individual suspected of having the disease, comprising a carrier means having in close confinement therein multiple container means, wherein a first container means contains a first detectable antibody that is immunoreactive with the 80-kDa isoform of μCANP, and is not immunoreactive with the 76-kDa and 78-kDa isoforms of μCANP, a second container means contains a second detectable antibody that is immunoreactive with the 76-kDa, 78-kDa and 80-kDa isoforms of μCANP, and further container means, wherein said further container means contain a standard serial dilution of the 76-kDa, 78-kDa, and 80-kDa isoforms in solution, sufficient to prepare standard curves for use in measuring the concentrations of the 76-kDa, 78-kDa and 80-kDa isoforms in a sample in order to calculate the ratio of the 76-kDa isoform to the 80-kDa isoform.

2. The kit of claim 1, wherein said first and second detectable antibodies are detectably labelled with different labels that can be discriminated on detection.

3. The kit of claim 1, further comprising a container means which contains a means for separating the 76-kDa, 78-kDa, and 80-kDa isoforms of μCANP.

* * * * *